(12) United States Patent
Wassmer et al.

(10) Patent No.: US 10,221,200 B2
(45) Date of Patent: Mar. 5, 2019

(54) QUATERNARY AMINO ALCOHOL FUNCTIONAL ORGANOSILICON COMPOUNDS, COMPOSITION CONTAINING THE LATTER AND THEIR PRODUCTION AND USE

(71) Applicant: Evonik Degussa GmbH, Essen (DE)

(72) Inventors: Christian Wassmer, Hausen (DE); Burkhard Standke, Loerrach (DE); Stefan Scharfe, Erlensee (DE); Christoph Batz-Sohn, Morris Plains, NJ (US); Andrea Heuschen, Floersbachtal (DE)

(73) Assignee: Evonik Degussa GmbH, Essen (DE)

( * ) Notice: Subject to any disclaimer, the term of this patent is extended or adjusted under 35 U.S.C. 154(b) by 173 days.

(21) Appl. No.: 15/586,954

(22) Filed: May 4, 2017

(65) Prior Publication Data
US 2017/0233416 A1 Aug. 17, 2017

Related U.S. Application Data

(62) Division of application No. 13/809,255, filed as application No. PCT/EP2011/059607 on Jun. 9, 2011, now Pat. No. 9,796,738.

(30) Foreign Application Priority Data

Jul. 9, 2010 (DE) .................. 10 2010 031 178

(51) Int. Cl.
| | | |
|---|---|---|
| C07F 7/08 | (2006.01) | |
| C07F 7/10 | (2006.01) | |
| C07F 7/18 | (2006.01) | |
| C08G 77/26 | (2006.01) | |
| C08L 83/04 | (2006.01) | |
| D21H 19/62 | (2006.01) | |
| B41M 5/52 | (2006.01) | |

(52) U.S. Cl.
CPC .............. *C07F 7/10* (2013.01); *B41M 5/529* (2013.01); *C07F 7/0836* (2013.01); *C07F 7/0838* (2013.01); *C07F 7/1804* (2013.01); *C08G 77/26* (2013.01); *C08L 83/04* (2013.01); *D21H 19/62* (2013.01)

(58) Field of Classification Search
None
See application file for complete search history.

(56) References Cited

U.S. PATENT DOCUMENTS

| | | | |
|---|---|---|---|
| 4,005,028 A | 1/1977 | Heckert et al. | |
| 4,013,573 A | 3/1977 | Leikhim et al. | |
| 5,051,129 A | 9/1991 | Cuthbert et al. | |
| 5,885,341 A | 3/1999 | Standke et al. | |
| 6,255,513 B1 | 7/2001 | Standke | |
| 6,641,870 B2 | 11/2003 | Bartkowiak et al. | |
| 6,767,982 B2 | 7/2004 | Standke et al. | |
| 7,834,073 B2 | 11/2010 | Standke et al. | |
| 8,039,110 B2 | 10/2011 | Jenkner et al. | |
| 8,101,682 B2 | 1/2012 | Standke | |
| 8,188,266 B2 | 5/2012 | Edelmann et al. | |
| 8,298,679 B2 | 10/2012 | Albert et al. | |
| 8,394,972 B2 | 3/2013 | Wassmer et al. | |
| 8,481,165 B2 | 7/2013 | Edelmann et al. | |
| 8,864,895 B2 | 10/2014 | Albert et al. | |
| 2002/0008011 A1 | 1/2002 | Sonnenschein et al. | |
| 2003/0175451 A1 | 9/2003 | Wickramanayake et al. | |
| 2004/0022946 A1 | 2/2004 | Vincent et al. | |
| 2004/0219311 A1 | 11/2004 | Wickramanayake et al. | |
| 2008/0206572 A1 | 8/2008 | Edelmann et al. | |
| 2009/0005518 A1 | 1/2009 | Just et al. | |
| 2009/0007818 A1 | 1/2009 | Militz et al. | |
| 2009/0028912 A1 | 1/2009 | Dave | |
| 2009/0035490 A1 | 2/2009 | Wickramanayake et al. | |
| 2010/0209719 A1* | 8/2010 | Borup .................... | C08G 77/26 428/447 |
| 2011/0259240 A1 | 10/2011 | Jenkner et al. | |
| 2012/0006228 A1 | 1/2012 | Scharfe et al. | |
| 2012/0037040 A1 | 2/2012 | Standke et al. | |
| 2012/0321803 A1 | 12/2012 | Borup et al. | |

FOREIGN PATENT DOCUMENTS

| | | |
|---|---|---|
| DE | 2009040281 A1 | 4/2009 |
| GB | 2 403 406 | 1/2005 |
| JP | 2011046642 A | 3/2011 |

OTHER PUBLICATIONS

International Search Report dated Jan. 11, 2012 in PCT/EP11/59607 Filed Jun. 9, 2011.
Michal Dutkiewicz, et al., "Functionalization of Polyhedral Oligomeric Silsesquioxane (POSS) via Nucleophilic Substitution" Synthesis 2009, No. 12, 2009, pp. 2019-2024.

* cited by examiner

*Primary Examiner* — Melvin C. Mayes
*Assistant Examiner* — Stefanie J Cohen
(74) *Attorney, Agent, or Firm* — Grüneberg and Myers PLLC

(57) ABSTRACT

The invention relates to novel quaternary amino alcohol functional organosilicon compounds, aqueous compositions containing the latter, and a method for their production, in particular in the form of oligomers and polymers which can be present in the partially or fully hydrolyzed form and are in particular water-soluble. The compositions comprise only an extremely small portion of VOCs. The invention further relates to their use, preferably in the production of inkjet photographic papers.

17 Claims, No Drawings

QUATERNARY AMINO ALCOHOL FUNCTIONAL ORGANOSILICON COMPOUNDS, COMPOSITION CONTAINING THE LATTER AND THEIR PRODUCTION AND USE

CROSS REFERENCE TO RELATED APPLICATION

This application is a divisional of U.S. application Ser. No. 13/809,255, filed on Jan. 9, 2013, now U.S. Pat. No. 9,796,739 which is a National Stage Entry of PCT/EP2011/059607, filed on Jun. 9, 2011, and claims priority to German Patent Application No. 10 2010 031 178.2, filed on Jul. 9, 2010.

The invention relates to new quaternary-amino alcohol-functional, organosilicon compounds, to aqueous compositions comprising them, and to processes for their preparation, more particularly in the form of oligomers and polymers, which may be in partly hydrolyzed to fully hydrolyzed form, and more particularly are water-soluble. The compositions have an extremely low VOC fraction. Further described is their use, more particularly—though not exclusively—for cationic modification of inorganic or polar organic surfaces, as for example fillers, pigments, glass, mineral and ceramic surfaces, synthetic and natural polar materials, such as, for example, polyesters, polyamides, wool, silk, cellulose, lignocellulose, wood, proteins, sugars, polysaccharides, and the like, which may also be present in particulate form or fiber form, in the cm, mm, micronized or else nanometric range, in papercoating slips, for cationization of inkjet coatings, preferably in the production of inkjet photographic papers, for finishing fiber materials and/or textiles, for improving the colorability of substrates, as for example in the case of textile fibers, yarns, paper, films or else correspondingly coated substrates, for inhibiting or suppressing the growth of microorganisms or of an electrostatic charge buildup, to give but a few particularly advantageous possibilities for application.

Generally speaking, organofunctional alkoxysilanes with quaternary nitrogen functionality, i.e., with a cationic group comprising an organofunctionalized nitrogen, have been known for some time. The quaternary nitrogen has a cationic functionality independently of the pH. Their preparation to date was possible only via costly and inconvenient processes, as for example under elevated pressure in an autoclave. A further disadvantage of these alkoxysilanes is the release of hydrolysis alcohols into the environment when using the known water-based application solutions.

The preparation of cationic organosilanes and their partial use in aqueous phases is reported in the documents which follow. DE 881654 discloses the preparation of quaternary silanes in an autoclave under anhydrous conditions. Further processes are disclosed by NL 6517163 for preparing quaternary methylaryl silanes; DE 1262272 discloses the preparation of corresponding silicones. DE 2221349, DE 2648240, U.S. Pat. No. 4,035,411, U.S. Pat. No. 4,005,118 and U.S. Pat. No. 4,005,119 disclose processes for preparing quaternary silanes.

WO 2008/004243 discloses water-soluble silanes with quaternary amino functionality. The water solubility is achieved by esterification with glycols, which in the course of the hydrolysis, i.e., of the "dissolution" of the silanes in water, are released and so give rise to a considerable contamination of the aqueous solution with additional organic components, which are commonly viewed as organic solvents.

The use of quaternary amino-functional alkoxysilanes for inhibiting the growth of microorganisms is described by DE 2222997, DE 2229580 and DE 2408192. Improved colorability of materials which are difficult to color, such as Teflon or else leather, through use of corresponding silanes is disclosed by GB 882067. The preparation of quaternary-functionalized organosilanes takes place in each case in aprotic organic solvents or under moisture exclusion and elevated pressure. The silanes prepared by these processes, or aqueous formulations of said silanes, contain large quantities of solvent. In many applications this leads to considerable disadvantages, such as a low flashpoint, necessitating explosion protection measures, or environmental damage caused by a high VOC burden.

WO 2008/076839 uses a commercially available quaternary silane (AEM 5772, Aegis antimicrobial agent, active ingredient: 3-(trimethoxysilyl)propyldimethyl-octadecylammonium chloride), containing 12% of methanol. U.S. Pat. No. 4,845,256 discloses a process for preparing quaternary silanes alkaline earth metal iodide catalysts for the reaction of chloroalkyl-functional alkoxysilanes and tertiary amines. The process described proceeds under atmospheric pressure at a temperature of 100° C., but is disadvantageous in two respects. First, alkaline earth metal iodides, which are problematic for the environment, are used in considerable quantities, and secondly the aqueous application solutions include considerable quantities of VOC, such as hydrolysis methanol and glycols, which are used in the process there and remain in the application solution. In an aqueous application solution, the product described in example 1 generates more than 50% of VOC (based on the as-used solution of the quaternary methoxysilane [3-(trimethoxysilyl)propyldecyldimethylammonium chloride] in solution in propylene glycol monomethyl ether).

The documents below disclose the use of cationic amino-functional silanes for the cationization of inkjet paper applications.

WO 2005/009745 A2 discloses cationic aluminum oxide particles with amino-functional silanes. US 20030175451 relates to the coating of silica with silanes for the purpose of improving performance in inkjet applications. US 20050170109 discloses the treatment of silica with amino-alkoxysilanes and use thereof for inkjet papers and DE 10 2007 012578 A1 discloses the preparation of cationic silica dispersions using primary, secondary or tertiary aminosilanes, and the use thereof for coatings. WO 2005/009745 A2, US 2005/170109 A1, and US 2003/175451 refer generally to the possibility of using a quaternary amino-functional alkoxysilane, such as trimethoxysilanepropyl-N,N,N-trimethylammonium chloride, or a N,N,N-tributylammonium chloride-substituted silane. Concrete examples are not disclosed.

DE 102007040802 A1 describes the successful use of low-VOC, protonated amino-functional siloxane systems containing silanol groups (Hydrosils) in the cationization of papercoating slips. The protonation of the amino function in these systems is heavily pH dependent. Consequently, the performance of these applications is still in need of improvement. The processing properties of papercoating slips are governed by their viscosity and solids content. The higher the viscosity, the greater the cost and inconvenience of processing, although at the same time a high solids content is desired for the systems for capacity reasons.

DE 10 2009 002 477.8 or PCT/EP2010/053626 reveals the reaction of chloropropyltriethoxysilane and tetramethylethylenediamine for the preparation of siloxane systems.

There therefore continues to be a need for reduced-VOC quaternary-amino-functional, organosilicon compounds, which allow the setting of a low viscosity in conjunction with high solids content for dispersions, as for example silica dispersions, more particularly papercoating slips. The water solubility thereof and VOC content of the organosilicon compounds ought preferably to be improved relative to known systems, and silica dispersions with a low coarse fraction ought preferably to be accessible.

The problem addressed by the present invention was that of providing VOC-reduced, quaternary-amino alcohol-functional, organosilicon compounds, and compositions comprising them, and VOC-containing intermediates thereof, and also an economic process for their preparation, which preferably allows the desired viscosity and the solids content to be set economically in the process.

The problem is solved in accordance with the invention as detailed in the claims. More particularly, the problem is solved by the quaternary-amino alcohol-functional, organosilicon compounds of the invention and also by the comprising composition in accordance with the features of the independent claims, and also by the preparation processes of the invention in the independent claims. Preferred embodiments are set out in the dependent claims and also in the description.

The problem has surprisingly been solved by reacting haloalkyl-functional alkoxysilanes with tertiary amino alcohols in the presence of or with the addition of a defined amount of water, or carrying out reaction waterlessly to start with and subsequently with a defined amount of water, and at least partly removing the hydrolysis alcohol formed, the hydrolysis alcohol preferably being removed substantially completely. The quaternization reaction and at least partial hydrolysis and optional partial condensation that take place advantageously are carried out under temperature control—in other words, according to the requirement, heating or cooling takes place, and the reaction mixture is also stirred appropriately. In the course of this procedure, an originally tertiary-substituted nitrogen atom in the amino alcohol is transformed into a quaternary nitrogen atom, more particularly with formation of inventively obtainable oligomeric and/or polymeric, quaternary-amino-functional organosilicon compounds, which are elucidated in more detail below. A particular surprise and advantage is that there is no need to use a catalyst for the quaternization reaction, for the hydrolysis and/or condensation. Moreover, with regard to the viscosity of the present systems, it was a surprise and advantage that no esters of the silanol groups with amino alcohol groups are formed under the process conditions.

The invention advantageously enables the provision of new VOC-reduced (volatile organic compound) quaternary-amino alcohol-functional, organosilicon compounds, which advantageously can be provided in high yield and under atmospheric pressure. The organosilicon compounds of the invention may have linear, branched and/or cyclic structures and/or structural regions with M, D, and/or T structures. Quaternary-amino alcohol-functional, organosilicon compounds of the invention and also corresponding aqueous compositions which comprise at least one of the quaternary-amino alcohol-functional, organosilicon compounds of the invention can be employed advantageously, with particular advantage for the provision of very low-VOC, low-viscosity silica dispersions for the production of papercoating slips, and more particularly dispersions of this kind with a comparatively low coarse fraction.

A further surprise associated with the reaction according to the invention is that the stated reactions, such as quaternization, hydrolysis, and preferably condensation, can be carried out almost simultaneously in a reaction mixture at relatively low reaction temperatures of below 100° C. and hence with particular advantage. A further particular advantage of the process of the invention is that the reaction can proceed at these relatively low temperatures under atmospheric pressure. In the process of the invention it is therefore possible, preferably, to do without the use of autoclaves which are expensive and inconvenient to operate, since, depending on the tertiary amino alcohols used and on their boiling point, the reaction is carried out advantageously under atmospheric pressure, if the boiling point of the amines is above the reaction temperature. The boiling point of the tertiary amino alcohols used, more particularly those of the formula III, is preferably, as elucidated below, above 85° C., more preferably above 100° C., more particularly above 120° C.

Thus it is particularly surprising that not only the quaternization reaction on the haloalkyl group of the haloalkyl-functional silane of the formula II that is used, but also the hydrolysis and also the condensation or co-condensation of the compounds II and/or IV present in the reaction mixture, and/or their hydrolysis products, proceeds not only simultaneously, i.e. in the form of a one-pot reaction, but furthermore, largely selectively as well.

The invention provides quaternary-amino alcohol-functional, organosilicon compounds, comprising quaternary-amino alcohol-functional silanols and also quaternary-amino alcohol-functional siloxanol oligomers with Si—O-crosslinked structural elements (hereinafter also called, for short, silanols and also siloxanol oligomers), which form catenate, cyclic and/or crosslinked structures and which are obtainable from a reaction of at least one silane of the formulae II, IV or at least one hydrolysis, condensation or co-condensation product starting from silanes of the formula II and/or IV, water and at least one amino alcohol of the formula III and optionally the hydrolysis alcohol formed in this reaction is at least partly removed from the system, where at least one structure of said quaternary-amino alcohol-functional, organosilicon compounds corresponds in idealized form to the general formula I,

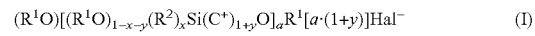

where C⁺ in formula I is independently a group of the formula V

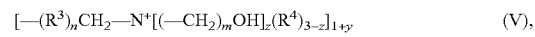

in formula I, $R^1$ independently of one another are hydrogen or a linear, branched or cyclic alkyl group having 1 to 8 C atoms, more preferably $R^1$ is substantially hydrogen and optionally a corresponding alkyl group, $R^2$ are identical or different and $R^2$ is a linear, branched or cyclic alkyl group having 1 to 8 C atoms or is an aryl, arylalkyl or acyl group, in formula V $R^3$ are identical or different and $R^3$ is a linear, branched or cyclic alkylene group having 1 to 18 C atoms, $R^4$ are identical or different and $R^4$ is a group comprising C1 to C16 atoms, more particularly $R^4$ is a hydrocarbon group, preferably an alkyl group having 1 to 16 C atoms, more preferably having 1 to 7 C atoms, in formulae I and V, independently, n is 0 or 1, m is an integer between 1 and 16 and z is 1 or 2 or 3, and Hal is chloro or bromo, and x is 0 or 1, y is 0 or 1 and (x+y) is 0 or 1, and a is greater than or equal to 1, more particularly greater than or equal to 2, more particularly greater than or equal to 4, where the silane of the formula II is a haloalkylsilane, $$(R^1O)_{3-x-y}(R^2)_x Si[(R^3)_n CH_2 Hal]_{1+y} \quad (II),$$

and the silane of the formula IV is a quaternary-amino alcohol-functional, organosilicon compound $$(R^1O)_{3-x-y}(R^2)_x Si[(R^3)_n CH_2 - N^+[-(CH_2)_m OH]_z(R^4)_{3-z}]_{1+y'} \cdot (1+y)[Hal^-] \quad (IV),$$

and the amino alcohol corresponds to the formula III, $$[HO-(CH_2)_m-]_z N(R^4)_{3-z} \quad (III),$$

where in the formulae II, III and/or IV, independently groups $R^1$ are identical or different and $R^1$ is a hydrogen, a linear, branched or cyclic alkyl group having 1 to 8 C atoms, or an aryl, arylalkyl or acyl group, groups $R^2$ are identical or different and $R^2$ is a linear, branched or cyclic alkyl group having 1 to 8 C atoms or is an aryl, arylalkyl or acyl group, $R^3$, $R^4$, Hal and also n, m and z, independently of one another, are as defined above, and x is 0, 1 or 2, y is 0, 1 or 2 and (x+y) is 0, 1 or 2.

Preferred siloxanol oligomers, more particularly of the general formula I shown only in idealized form, have a high fraction of D structures and T structures of in each case more than 10% ($^{29}$Si-NMR). They may preferably have between 30% to 60% D structures and 30% to 60% T structures, more particularly of in each case around 40 to 55%, more preferably in each case around 40% to 50%, with 100% being achieved in total with silanes and with M structures, which are present only to a minor extent. (Regarding the definition of M, D, and T structures, see Walter Noll, Chemie and Technologie der Silicone [Chemistry and Technology of Silicones], 1968, Verlag Chemie GmbH, Weinheim, chapter 1).

Here m is preferably 1, 2, 3, 4, 5, 6 or 7 and $R^4$ is a group comprising 1, 2, 3, 4, 5, 6 or 7 C atoms, more preferably m is 1, 2 or 3, inventively m is 2; and $R^4$ is a linear, branched or cyclic alkyl group having 1 to 16 C atoms, more particularly an alkyl group having 1 to 7 C atoms, preferably an alkyl group having 1 to 6 C atoms, more preferably having 1 to 4 C atoms, and this group furthermore may be substituted, in which case optionally two groups $R^4$ are in turn linked to one another and form a ring system with the nitrogen of the tertiary amine.

In accordance with the invention, the quaternary-amino alcohol-functional organosilicon compounds in the form of siloxanol oligomers, such as formula I, where with particular preference $R^1$ corresponds substantially to hydrogen, are water-soluble; advantageously the compounds of the formula IV are water-soluble as well.

In accordance with the invention, use is made as amino alcohols of the formula III preferably of N,N-dimethylethanolamine, N,N-diethylethanolamine, N-methyldiethanolamine, N-ethyldiethanolamine, triethanolamine or at least two of the aforementioned compounds.

The pure quaternization reaction of compounds of the formula II or as per component A, and of the tertiary amino alcohol of the formula III as per component B, to give at least one quaternary-amino alcohol-functional, organosilicon compound of the formula I and/or IV is set out in a model basis below, with the formulae II and III being defined as above:

$$(R^1O)_{3-x-y}(R^2)_x Si[(R^3)_n CH_2 Hal]_{1+y} + [HO-(CH_2)_m-]_z N(R^4)_{3-z} \rightarrow \quad (II)(III)$$

$$(R^1O)_{3-x-y}(R^2)_x Si[(R^3)_n CH_2 - N^+[-(CH_2)_m OH]_z(R^4)_{3-z}]_{1+y'} \cdot (1+y)[Hal^-] \quad (IV).$$

Furthermore, during the reaction, by hydrolysis and also condensation of compounds of the formulae II and/or resultant quaternization products (IV), it is possible for what are called oligomeric and/or polymeric, quaternary, amino alcohol-functional, organosilicon compounds, comprising silanols and/or substantially siloxanol oligomers, to be formed as are elucidated below. Here, of course silanols and/or siloxanol oligomers that are present may also contain Si-bonded alkoxy groups; in this regard, see also formula I.

Hence in accordance with chemical understanding it is assumed that under the reaction conditions according to the invention, the reaction of compounds of the formulae II and III proceeds with quaternization and at least partial hydrolysis, as illustrated on a model basis below using 3-chloropropyltriethoxysilane (CPTEO) and N,N-dimethylethanolamine, without confining the model thereto.

Quaternization and partial or complete hydrolysis:

$$Cl-(CH_2)_3-Si(OEt)_3 + [HO-(CH_2)_2-]N(CH_3)_2 + H_2O \rightarrow (EtO)_2(HO)Si[-(CH_2)_3-N^+ [-(CH_2)_2OH](CH_3)_2].Cl^- + EtOH$$

$$Cl-(CH_2)_3-Si(OEt)_3 + [HO-(CH_2)_2-]N(CH_3)_2 + 2H_2O \rightarrow (EtO)(HO)_2Si[-(CH_2)_3-N^+ [-(CH_2)_2OH](CH_3)_2].Cl^- + 2EtOH$$

$$Cl-(CH_2)_3-Si(OEt)_3 + [HO-(CH_2)_2-]N(CH_3)_2 + 3H_2O \rightarrow (HO)_3Si[-(CH_2)_3-N^+ [(-CH_2)_2OH](CH_3)_2].Cl^- + 3EtOH$$

Condensation:

$$x(HO)_3Si[(-CH_2)_3-N^+[-(CH_2)_2OH](CH_3)_2].Cl^- \rightarrow [(HO-)_2Si[-(CH_2)_3-N^+[-(CH_2)_2OH](CH_3)_2]]-[O-Si[-(CH_2)_3-N^+[-(CH_2)_2OH](CH_3)_2](OH)]_{x-2}-[O-Si[-(CH_2)_3-N^+[-(CH_2)_2OH](CH_3)_2](OH)_2].xCl^- + xH_2O$$

Depending on the degree of hydrolysis, there may also be alkoxy groups instead of hydroxyl groups. In that case x may be a number form 2 to ∞.

The invention also provides a process for preparing a composition comprising quaternary-amino alcohol-functional, organosilicon compounds, comprising quaternary-amino alcohol-functional silanols and also siloxanol oligomers, and also compositions obtainable by this process, preferably a composition comprising quaternary-amino alcohol-functional siloxanol oligomers, by reacting
as component A
(i) at least one haloalkyl-functional alkoxysilane of the general formula II $$(R^1O)_{3-x-y}(R^2)_x Si[(R^3)_n CH_2 Hal]_{1+y} \quad (II),$$

in which groups $R^1$ are identical or different and $R^1$ is a hydrogen, a linear, branched or cyclic alkyl group having 1 to 8 C atoms, or an aryl, arylalkyl or acyl group, and groups $R^2$ are identical or different and $R^2$ is a linear, branched or cyclic alkyl group having 1 to 8 C atoms or is an aryl, arylalkyl or acyl group, groups $R^3$ are identical or different and $R^3$ is a linear, branched or cyclic alkylene group having 1 to 18 C atoms, n is 0 or 1 and Hal is chloro or bromo, and x is 0, 1 or 2, y is 0, 1 or 2 and (x+y) is 0, 1 or 2,
or
(ii) a hydrolysis or condensation product of at least one alkoxysilane of the aforementioned general formula II, hydrolysates and/or homocondensate or mixtures of at least two alkoxysilanes of the formula II thereof,
or
(iii) a mixture of at least one alkoxysilane of the aforementioned general formula II and a hydrolysis and/or condensation product of at least one alkoxysilane of the aforementioned general formula II with a tertiary amino alcohol of the general formula III as component B,

in which groups $R^4$ are identical or different and $R^4$ is a group comprising C1 to C16 atoms, m is an integer between 1 and 16, more particularly is a hydrocarbon group or alkyl group as defined above, and z is 1 or 2 or 3; preferably m is 1 to 7 and $R^4$ is a group comprising C1 to C7 atoms, more preferably m is 1, 2 or 3, inventively m is 2; and $R^4$ is a linear, branched or cyclic alkyl group having 1 to 16 C atoms, more particularly an alkyl group having 1 to 7 C atoms, preferably an alkyl group having 1 to 6 C atoms, more preferably having 1 to 4 C atoms, which may, furthermore, be substituted, in which case optionally two groups $R^4$ are internally linked to one another and form a ring system with the nitrogen of the tertiary amine; with particular preference the amino alcohol is N,N-dimethylethanolamine, N,N-diethylethanolamine, N-methyldiethanolamine, N-ethyldiethanolamine, triethanolamine or a mixture comprising at least two of the compounds, wherein the process is carried out in at least one step in the presence, and/or more particularly with addition, of a defined amount of water, and optionally the hydrolysis alcohol formed is removed at least partly from the system; preferably hydrolysis alcohol formed and also any solvent added are substantially completely removed.

In accordance with preferred process variants, the reaction of component A and of component B is carried out in the presence of a defined amount of water or component A is reacted with component B and the product is subsequently hydrolyzed in the presence of a defined amount of water; preferably, in component A, more particularly of the formula II, $R^1$ is alkyl having 1 to 4 C atoms, acyl, and $R^3$ is a linear alkylene group having 1, 2, 3, 4, 5, 6, 7 C atoms, preferably having 2 C atoms.

In accordance with the invention, use is made as component A of at least one silicon compound selected from 3-chloropropyltrimethoxysilane, 3-chloropropyltriethoxysilane, 3-chloropropylmethyldimethoxysilane, 3-chloropropylmethyldiethoxysilane, 3-chloropropyldimethylethoxysilane or 3-chloropropyldimethylmethoxysilane or a hydrolysis or condensation product of the aforementioned alkoxysilanes.

In the process of the invention it is particularly preferred to use a haloalkyl-functional silane of the formula II selected from the following group: chloropropyltrimethoxysilane, chloropropyltriethoxysilane, chloropropylmethyldimethoxysilane and chloropropylmethyldiethoxysilane and/or the hydrolysis and/or condensation product thereof.

In preferred processes, $R^3$ in formula II or IV is a linear, branched and/or cyclic alkylene having 1 to 18 C atoms, more particularly a methylene (—$CH_2$—), ethylene [—$(CH_2)_2$—], propylene [—$(CH_2)_3$—], butylene [—$(CH_2)_4$— or —$(CH_2)CH(CH_3)(CH_2)$—], and n=0 with Hal being chloro. With particular preference the moiety —$[(R^3)_nCH_2Hal]$ is a chloromethylene, chloroethylene, 3-chloropropylene, 2-chloropropylene, 2-chloroisopropylene, chlorobutylene, chloroisobutylene, chloropentyl, chlorohexyl, chlorocyclohexyl, chloroheptyl, chlorooctyl, chloro-n-octyl, chlorocyclooctyl group. Other haloalkylsilanes of the formula II that can be used in the process of the invention are selected more particularly from the group consisting of 3-chloropropyltrimethoxysilane, 3-chloropropyltriethoxysilane, 3-chloropropyltripropoxysilane, chloropropylmethyldimethoxysilane, chloropropylmethyldiethoxysilane, chloropropyldimethylethoxysilane, chloropropyldimethylmethoxysilane, chloroethyltrimethoxysilane, chloroethyltriethoxysilane, chloroethylmethyldimethoxysilane, chloroethylmethyldiethoxysilane, chloroethyldimethylmethoxysilane, chloroethyldimethylethoxysilane, chloromethyltriethoxysilane, chloromethyltrimethoxysilane, chloromethylmethyldimethoxysilane, chloromethylmethyldiethoxysilane, chloromethyldimethylmethoxysilane, chloromethyldimethylethoxysilane, 2-chloroisopropyltris(methoxyethoxy)silane, 3-chloropropylcyclohexyldiethoxysilane, 3-chloroisobutyltrimethoxysilane, 3-chloroisobutyltriethoxysilane, 3-chloropropylcyclohexyldimethoxysilane, 3-bromoisoropyldiethylcyclohexoxysilane, 3-chloropropylcyclopentyldieneethoxysilane, 3-bromoisobutyltrimethoxysilane, 3-chloroisobutylbis(ethoxyethoxy)methylsilane, 4-bromo-n-butyltriethoxysilane, 4-chloro-n-butyldiethoxycyclopentylsilane, 5-chloro-n-pentyltri-n-butoxysilane, 5-bromo-n-pentyltriethoxysilane, 4-bromo-3-methylbutyldimethoxyphenylsilane, 5-bromo-n-pentyltri-n-butoxysilane, 5-chloro-n-pentyltriethoxysilane, 6-chloro-n-hexylethoxydimethylsilane, 6-bromo-n-hexylpropyldipropoxysilane, 6-chloro-n-hexyldiethoxyethylsilane, 7-chloro-n-heptyltriethoxysilane, 7-chloroheptyldimethoxycycloheptylsilane, 7-bromo-n-heptyl-, diethoxycyclooctylsilane, 8-chloro-n-oxtyltriethoxysilane, 8-bromo-n-octyldimethylcyclohexoxysilane, 3-chloropropyldiethoxyphenylsilane, 3-chloropropylmethoxyethoxybenzylsilane, 3-bromopropyldimethoxybenzylsilane and/or the hydrolysis and/or homo- and/or co-condensation products thereof or, judiciously, 1,4-chlorophenyltrimethoxysilane, 1,4-chlorobenzyltriethoxysilane and chloromethyl-p-methylphenyltrimethoxysilane and/or the hydrolysis and/or homo- and/or co-condensation products thereof are used. Particular preference is given to using pure chloroalkyl-substituted alkoxysilanes in the process of the invention.

With particular advantage, in relation to the haloalkyl group of component A and to the tertiary nitrogen of component B, components A and B are used in a molar ratio of 2:1 to 1:100, more particularly of 2:1 to 1:10, preferably of 2:1 to 1:5, more preferably of about 1:1 to about 1:1.5. 1:1, in which case optionally first a ratio of 1:1 is set and subsequently in addition, per portion, about 0.2 of component B in relation to the component A present is added in 1 to 4 portions.

A process regime which has proven particularly advantageous is one in which water is used in an amount of 0.5 to 500 mol per mole of silicon atoms present in component A, preferably in at least one of the hydrolysis steps 0.5 mol of water per mole of hydrolyzable alkoxy group on the silane of the formula II, in which case in total it is preferred more particularly to use 0.5 to 25 mol of water, preferably 5 to 25 mol of water per mole of silicon atoms in respect of component A used, more preferably 10 to 25 mol of water per mole of the silicon atoms, more particularly 12 to 25 mol of water per mole of silicon atoms.

In this context it is further of advantage if the water, more particularly in defined amounts, is metered continuously or discontinuously, in portions, into component A, optionally in a mixture with component B, or into the quaternary-amino alcohol-functional, organosilicon compound of the formula IV

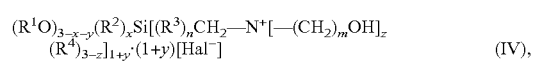

that is formed; preferably the water is added discontinuously with stirring, more preferably in portions, advantageously in 1 to 15 portions, more particularly in 2 to 12 portions, wherein formula IV $R^1$, $R^2$, $R^3$, $R^4$, x, y, z, n and m have the definition defined above, more particularly according to claim 2. With further preference, addition takes place in portions, in each case as a defined amount of water, of 0.5 to 4.0 mol of water per mole of silicon atoms, preferably around 1.0 to 2.0 mol of water per mole of silicon atoms, more preferably around 1.5 mol plus/minus 0.5 mol, and optionally a final portion with 5 to 25 mol of water per mole of silicon atoms is added.

Depending on the process regime, it has proven advantageous if the reaction is carried out in the presence of a solvent, more particularly an alcohol or an alcohol mixture or an alcohol/water mixture, with glycols also being included among the alcohols, preferably in the presence of the alcohol formed in the hydrolysis of the compound of formula II, more preferably in the presence of ethanol, methanol, n-propanol or isopropanol. In this case, the added solvent is suitably removed during the removal from the system of the hydrolysis alcohol formed during the reaction.

The hydrolysis alcohol formed during the reaction is removed substantially completely preferably by distillation, more particularly during the reaction itself. In accordance with one particularly preferred process regime, for instance, it is possible for the amount of hydrolysis alcohol and water, removed by distillation, in the azeotropic mixture to be compensated by additional addition of water.

Volatile solvents, such as an added solvent and/or the alcohol formed by hydrolysis in the reaction, i.e., any groups which can be hydrolyzed to volatile solvent, more particularly hydrolysis alcohol, are removed down to a level in the overall composition of below 12% by weight to 0% by weight, preferably by distillation in accordance with methods familiar to the skilled person. A composition is considered free from solvents if the amount of solvents in the overall composition has been adjusted to below 10% by weight to 0% by weight, more preferably below 5% by weight, very preferably below 2% by weight to 0.0001% by weight, more particularly 1 to 0.5% by weight, preferably 0.5 to 0.1% by weight, it being possible for the removal of volatile solvent to take place during the reaction and/or thereafter by distillation, more particularly under reduced pressure in the range from 0.1 to 1000 mbar, preferably from 80 to 300 mbar, more preferably in the range from 80 to 180 mbar. Suitably, however, the pressure may also be lowered from ambient pressure to a reduced pressure in the course of the reaction. The distillation may take place discontinuously or continuously by means of a distillation column, thin-film evaporator and also other apparatus familiar to the skilled person. In the distillation, it is preferred to distill until only water is still detectable at the top of the separating column. Water removed by distillation can be supplemented by renewed addition of water. At the end of the distillation, the desired final concentration of the solution can be set by adding further water.

In accordance with the process of the invention, the reaction is carried out advantageously under a pressure of 1 mbar to 100 bar, preferably at about 1 mbar to 1.1 bar, more preferably under ambient pressure (atmospheric pressure), and at a temperature of 20 and 150° C., preferably between 40 to 120° C., more preferably between 60 to 100° C., more particularly from 80 to 95° C.

Below, preferred process regimes for preparing the compositions are described in more detail, without confining the subject matter of the invention to these regimes; the skilled person knows of additional, customary process variations.

With regard to the implementation of the processes of the invention it has proven advantageous if, prior to the reaction of haloalkyltrialkoxysilane of the formula II with an amino alcohol of the formula III, more particularly of 3-chloropropyltriethoxysilane (CPTEO) with N,N-dimethylethanolamine, the haloalkyltrialkoxysilane is prehydrolyzed, and hydrolysis alcohol released is removed by distillation, as shown in example 5, for example, without restricting the process to that example. If there is no prehydrolysis of haloalkyltrialkoxysilane of the formula II, more particularly of CPTEO, prior to the reaction with the amino alcohol, more particularly with N,N-dimethylethanolamine, then it is advantageous to add the amino alcohol in excess in order to prevent extensive precipitation of CPTEO, as shown by way of example in example 3, without restricting the process to that example. Where necessary, excess amino alcohol, such as N,N-dimethylethanolamine, can be separated off distillatively. Generally speaking, in all processes, a haloalkyltrialkoxysilane of the formula II, more particularly CPTEO, that has not reacted completely with the amino alcohol of the formula III, such as N,N-dimethylethanolamine, can be precipitated in principle by addition of water, as in example 2, for example. Where the reaction of the haloalkyltrialkoxysilane of the formula II, more particularly of CPTEO, takes place with the amino alcohol of the formula III, such as N,N-dimethylethanolamine, at excessively high temperatures, as for example at temperatures of 140° C.-150° C., then this can result in intense discolorations of the product, as depicted in example 4, for example.

The invention also in particular provides process variants in which a) component A is introduced together with a solvent and a defined amount of water is added, component B is added, hydrolysis alcohol formed is removed at least partly from the system, and water is added in defined amounts, or b) component A is introduced and a solvent is added, a defined amount of water is added, component B is added, hydrolysis alcohol formed is removed at least partly from the system, and water is added in defined amounts, or c) component A is introduced and a solvent is added, a defined amount of water is added, hydrolysis alcohol formed is removed at least partly from the system, thereafter component B is added, and hydrolysis alcohol formed is removed at least partly from the system, a defined amount of water is added and hydrolysis alcohol formed is removed at least partly from the system, and water is added in defined amounts, or d) component A is reacted with component B at elevated temperature, and further component B is added in a defined amount, and subsequently a defined amount of water is added, hydrolysis alcohol formed is removed at least partly from the system, and water is added in defined amounts, or e) component A is introduced and a solvent is added, a defined amount of water is added, and hydrolysis alcohol formed is removed at least partly from the system, subsequently component B is added, and at elevated temperature a defined amount of water is added, and hydrolysis alcohol formed is removed at least partly from the system, and optionally water is added in defined amounts, or f) component A is introduced together with a solvent and a defined amount of water is added, hydrolysis alcohol formed is removed at least partly from the system, component B is added, hydrolysis alcohol formed is removed at least partly from the system, and water is added in defined amounts.

Further preference is given to the more specific process regimes, but without restricting the invention to them. Particularly preferred, therefore, are processes for preparing the compositions comprising quaternary-amino alcohol-functional, organosilicon compounds, more particularly of quaternary-amino alcohol-functional siloxanes of the compounds, such as of the idealized formula I, for example, in which a) component A is introduced together with a solvent, more particularly alcohol, such as ethanol or methanol, and a portion of a defined amount of water is added, more particularly about 1.5 mol of water per mole of silicon atoms, component B is added and is heated, more particularly under reflux, hydrolysis alcohol formed is removed at least partly under atmospheric pressure from the system, and water is added in defined amounts in portions, more particularly about a further 1 to 15 portions with in each case 0.5 to 3 mol, preferably in each case 1.5 mol of water per mole of silicon atoms, subsequently the hydrolysis alcohol is removed under reduced pressure and water is added until the amount of the hydrolysis alcohol in the overall composition is below 5% by weight; preferably the hydrolysis alcohol is distilled off and new water is added until the composition is substantially free from solvent or hydrolysis alcohol, or b) component A is introduced and a solvent is added, more particularly alcohol, preferably the alcohol formed during the hydrolysis, as, for example, ethanol or methanol, a portion of a defined amount of water is added, more particularly about 0.5 to 3.0 mol of water per mole of silicon atoms, preferably in each case 1.5 mol of water per mole of silicon atoms, consequently, preferably, prehydrolysis takes place, component B is added and the portion is heated, more particularly under reflux, hydrolysis alcohol formed is removed at least partly under atmospheric pressure from the system, preferably completely, and water is added in defined amounts in portions, more particularly about a further 1 to 15 portions with in each case 0.5 to 3 mol, preferably in each case 1.5 mol, of water per mole of silicon atoms, or c) component A is introduced and a solvent is added, more particularly alcohol, preferably the alcohol formed during the hydrolysis, as for example ethanol or methanol,
subsequently a portion of a defined amount of water is added, more particularly about 0.5 to 3.0 mol of water per mole of silicon atoms, preferably in each case 1.5 mol of water per mole of silicon atoms, preferably, therefore, prehydrolysis takes place, hydrolysis alcohol formed is removed at least partly under atmospheric pressure from the system after which component B is added, hydrolysis alcohol formed is optionally removed at least partly under atmospheric pressure from the system, and the reaction mixture is heated under reflux, a portion of a defined amount of water is added, and hydrolysis alcohol formed is removed at least partly under atmospheric pressure from the system, and water is added in defined amounts in portions, preferably completely, and water is added in defined amounts in portions, more particularly about a further 1 to 15 portions with in each case 0.5 to 3 mol, preferably in each case 1.5 mol, of water per mole of silicon atoms, or d) component A is reacted with component B at elevated temperature, and further component B is added in defined amounts discontinuously or continuously, until component A has reacted substantially completely with component B, more particularly to form the compound of the formula IV, thereafter a portion of a defined amount of water is added, and hydrolysis alcohol formed is removed at least partly under atmospheric pressure from the system, and water is added in defined amounts in portions, preferably completely, and water is added in defined amounts in portions, more particularly about a further 1 to 15 portions with in each case 0.5 to 3 mol, preferably in each case 1.5 mol, of water per mole of silicon atoms, or e) component A is introduced and a solvent is added, then a portion of a defined amount of water is added, more particularly about 0.5 to 3.0 mol of water per mole of silicon atoms, preferably in each case 1.5 mol of water per mole of silicon atoms, preferably, therefore, prehydrolysis takes place, and hydrolysis alcohol formed is removed under reduced pressure at least partly from the system, and subsequently component B is added in defined amounts discontinuously or continuously, and at elevated temperature at least one portion of a defined amount of water is added, more particularly as elucidated above, and hydrolysis alcohol formed is removed at least partly under atmospheric pressure or under reduced pressure from the system, and optionally water is added in defined amounts in portions, more particularly in 1 to 15 portions, as set out above.

In accordance with one further preferred alternative, the process can also be carried out by adding optionally a solvent, preferably an alcohol, more preferably methanol, ethanol, or isopropanol, to component A, prehydrolyzing component A with water in an amount of 0.5 to 3.0 mol of water per mole of the silicon atoms present, preferably with 0.5 to 2 mol of water per silicon atoms present, more preferably around 1.5 mol of water per mole of silicon atoms, adding component B, adjusting the reaction mixture present, at ambient pressure or reduced pressure, to a temperature of between 20 and 150° C., preferably around 40 to 120, more preferably around 60 to 100° C., and removing the hydrolysis alcohol formed at least partly, preferably substantially completely, from the reaction mixture, and also adding the solvent optionally used, and at the same time optionally water, in defined amount, optionally diluting the resultant composition with water, adjusting the solids content in the composition preferably to 0.1% to 99.9% by weight, and subsequently optionally admixing or contacting the composition with at least one further component from the series of pigments, fillers, binders, cross-linkers, optical brighteners, thickeners, rheological auxiliaries, coating auxiliaries or another auxiliary.

In the aforesaid processes it is particularly preferred if the composition is adjusted by addition of water to a viscosity of less than 1500 mPa s, preferably to a viscosity in the range from 1 to 300 mPa s, more preferably 1 to 100 mPa s, very preferably 5 to 60 mPa s, in accordance with the invention 5 to 20 mPa s. To the skilled person it is clear that the adjustment of the viscosity may take place in principle during the preparation and also at a later point in time, as, for example, prior to use.

The addition of the entire amount of water in one step for the reaction may lead to the formation of insoluble precipitates, which diminish the yield and which have to be removed by costly and inconvenient filtration for the purpose, for example, of producing solutions of the composition.

In the process, advantageously, in accordance with the invention, a silane of the formula II, more particularly a chloroalkyl-functional silane optionally the hydrolysis and/or condensation product thereof, is mixed with a tertiary amino alcohol of the formula III, optionally in the presence of a solvent, and in the presence of 0.5 to 200 mol of water per mole of silicon atoms there is a quaternization—on the nitrogen atom with formation of a compound of formula IV and/or I—and at least partial hydrolysis and optionally condensation (of the alkoxysilanes to silanol groups, followed by a condensation to form Si—O—Si bridges)—of the compounds of the quaternary-amino alcohol-functional, organosilicon compounds comprising siloxanol oligomers. The reaction may be carried out preferably in a kind of "one-pot reaction", batchwise for example, in which case hydrolysis alcohol is distilled off actually during the reaction and water can be supplemented by metering at substantially the same time. In this case, the pressure in the reaction vessel may also be lowered as the reaction time goes on; in other words the volatile organic components, more particularly the hydrolysis alcohol formed, are removed at least proportionally from the system by distillation under reduced pressure.

In the process of the invention it is also possible to carry out filtration, or for a composition obtained in accordance with the invention to be filtered, as and when required, in a conventional way, if cloudiness occurs.

In accordance with the invention, the reaction can be carried out without additional catalyst. It may, however, prove useful to add a hydrolysis and/or condensation catalyst as for example—but not exclusively—an organic or inorganic acid, such as formic acid, acetic acid, propionic acid, citric acid, hydrogen chloride, as a gas, concentrated or aqueous hydrochloric acid, boric acid, nitric acid, sulfuric acid, phosphoric acid, to name but a few. Correspondingly it is also possible at any time to add an organic or inorganic acid in order to set the pH of the composition or reaction mixture.

Furthermore, it may be preferable, as a further component in the process of the invention, to use metal oxides, preferably metal oxides having hydroxyl groups capable of condensation. These oxides are more particularly silica, fumed silica, precipitated silica, silicates, boric acid, titanium dioxide, aluminum oxide, aluminum oxide hydrate, ATH (aluminum trihydroxide, $Al(OH)_3$), magnesium hydroxide ($Mg(OH)_2$), cerium oxide, yttrium oxide, calcium oxide, iron oxides, zirconium oxide, hafnium oxide, boron oxide, gallium oxide, indium oxide, tin oxide, germanium oxide, and also corresponding hydroxides and oxide hydrates, and also mixtures of at least two of the aforementioned compounds with one another.

Volatile solvents or groups hydrolyzable to volatile solvents are considered to encompass alcohols, such as methanol, ethanol, isopropanol, n-propanol, and alkoxy groups, which hydrolyze to form alcohols, radicals containing acyloxy groups, and also the acetic acid or formic acid derived by hydrolysis, or else aryloxy groups, which may form phenols, and also glycols, and also partially etherified glycols such as ethylene glycol, diethylene glycol or methoxyethanol, which either are added to the formulation or are formed by hydrolysis of their silyl esters.

In the context of the invention, condensation products are understood to be both homo- and co-condensation products from the reaction of hydrolyzed alkoxysilanes, oligomeric or else polymeric organosilicon compounds containing Si—OH groups, and also condensation products with the participation of block co-condensates, of the initially in each case hydrolyzed and condensed compounds of the formulae II and IV, which subsequently as well may be reacted with amino alcohols to form completely quaternized block co-condensates.

The invention accordingly also provides a quaternary-amino alcohol-functional, organosilicon compound of the formula IV, as per the definition above for $R^1$, $R^2$, $R^3$, $R^4$, Hal, x, y, z, n and m of the formula IV or as per claim 1, more particularly as an intermediate for preparing the quaternary-amino alcohol-functional siloxanol oligomer shown in idealized form as formula

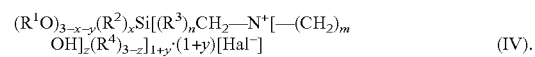

(IV).

Likewise provided by the invention is a process for preparing a quaternary-amino alcohol-functional, organosilicon compound of the formula IV

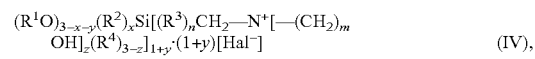

(IV), by reacting the haloalkyl-functional silane of the formula II, as defined above or as in claim 2, with an amino alcohol of the formula III, as defined above or as in claim 2, to give a compound of the formula IV, as defined above or as in claim 1. More particularly, it is possible to react a silane of the formula II with a silane of the formula III at an elevated temperature, optionally in the presence of a preferably inert solvent, and further silane is added in defined amounts, discontinuously or continuously, until the silane of the formula II has undergone substantially complete reaction with the amino alcohol of the formula III. Working up may take place in accordance with the methods and techniques customary to the skilled person, such as, for example, distillation, optionally with a thin-film evaporator.

The invention accordingly further provides as well a composition comprising quaternary-amino alcohol-functional, organosilicon compounds, more particularly quaternary-amino alcohol-functional siloxanol oligomers, as in accordance with the idealized formula I, and compounds of the formula IV, and water, said composition being obtainable by one of the above-elucidated processes or by a process. In this context it is particularly preferred if the quaternary-amino alcohol-functional, organosilicon compounds obtainable in the process are water-soluble, including more particularly the siloxanol oligomers.

The compositions of the invention are distinguished advantageously by a low viscosity in conjunction with high solids content, as demonstrated by the working examples. This combination of low viscosity and high solids content is a necessary prerequisite for a high capacity in the production of coatings. At the same time, the compositions of the invention are substantially VOC-free. Accordingly, the compositions of the invention exhibit significantly enhanced performance relative to known compositions. Compositions comprising alcohol, however, are not thereby fundamentally ruled out.

The composition obtained in accordance with the invention is generally liquid and of low to moderate viscosity, with the viscosity more particularly being below 1500 mPa s to 0.001 mPa s, preferably between 1000 and 1 mPa s, more preferably below 300 mPa s, preferably below 200 mPa s, more preferably below 100 mPa s, better still between 100 mPa s and 1 mPa s; further preference is given to ranges from 50 to 1 mPa s, more particularly from 20 and 5 mPa s (the viscosity is determined in accordance with DIN 53015).

It is further preferred if the compositions have a solids content in the composition of 0.1% to 99.9% by weight, preferably 0.5 to 90% by weight, more particularly of 5% to 70% by weight, preferably of 7% to 60% by weight, more preferably of 30% to 60% by weight, with all the constituents in the composition making 100% by weight in total.

It is particularly preferred here if the compositions have a solids content preferably of 7% to 60% by weight, more preferably of 30% to 60% by weight, preferably of 40% to 60% by weight and the composition at the same time has a viscosity of <1500 mPa s, preferably <1000 mPa s, more preferably 1 to 300 mPa s, more particularly of 1 to 100 mPa s, better still of 5 to 20 mPa s. One particularly preferred composition has a solids content of 30% to 60% by weight with a viscosity of 5 to 20 mPa s. Compositions of the invention have a solids content of 40% to 60% by weight, at viscosity of 5 to 20 mPa s.

A composition is preferred, moreover, when it has a total nitrogen content of 0.1% to 15% by weight, more particularly of 1.0% to 4.0% by weight with a viscosity of 1 to 100 mPa s, more preferably 5 to 20 mPa s, and optionally a pH in the range from 5.0 to 11.0, preferably from 6.0 to 9.0.

A composition may be further preferred if it additionally or alternatively has a water content of 0.0999 to 99.9% by weight and a volatile solvent/hydrolysis alcohol content in the overall composition of below 12% by weight to 0% by weight, preferably below 1 to 0.0001% by weight, with all of the constituents in the composition making 100% by weight in total.

It may be preferable, furthermore, if a composition comprises at least one other of the following components from the series pigments, fillers, binders, crosslinkers, optical brighteners, coating auxiliaries or other auxiliaries.

In accordance with the invention the present composition is substantially free from volatile solvents, preferably from hydrolysis alcohol, and more particularly, on crosslinking, no longer releases any hydrolysis alcohol, and more particularly it has a flash point of above 90° C.

The claimed compositions are substantially stable in storage. That is, they do not exhibit any visible changes such as cloudiness or sedimentation or gelling within two weeks, preferably 3 months, more preferably 1 year.

Prior to use, the compositions of the invention and also the end products of the invention can as and when necessary be diluted advantageously to a content of between 10% to 0.01% by weight, preferably to 5% to 0.1% by weight, with water or other solvents or else mixtures thereof.

The invention also provides a formulation comprising a composition of the invention, more particularly aqueous composition, which further comprises at least one of the following components from the series pigments, binders, crosslinkers, optical brighteners, coating auxiliaries, active ingredient and/or auxiliary and/or filler.

The compositions of the invention can also be used with very good suitability in inkjet coatings, more particularly for high gloss coats on paper.

Likewise provided by the invention is the use of the quaternary-amino alcohol-functional, organosilicon compound or of a composition for modification, treatment and/or production of formulations, substrates, articles, organic or inorganic materials, composite materials, papercoating slips, inkjet applications, preferably for producing inkjet photographic papers, papercoating materials, paper, textiles, fillers, biocidally, fungicidally and/or virucidally acting formulations, biocidally, fungicidally and/or virucidally acting coatings, for finishing of fiber materials, yarns and/or textiles, for textile impregnation, for antistaticization of surfaces, more particularly of sheetlike, fibrous, woven, granular and/or pulverulent materials, hence more particularly for the cationic modification of inorganic or polar organic surfaces, as for example fillers, pigments, glass, mineral, and ceramic surfaces, natural and synthetic polar substances, such as, for example, polyesters, polyamides, wool, silk, cellulose, lignocellulose, wood, proteins, sugars, polysaccharides, and the like, which may also be present in particulate form or fiber form, in the cm, mm, micronized or else nanometer range.

One preferred application for the compositions of the invention is the production of papercoating slips. For this purpose it is suitable first to prepare an aqueous silica dispersion and to treat it with the silane system of the invention, usually under high shearing forces applied using dispersing equipment customary in the industry. For optimum results, a mean aggregate size of 140-160 nm is desirable. Within a system, higher degrees of filling lead in the course of dispersing to a decrease in the average particle size. The resulting silanized silica dispersion is notable advantageously for a high solids content, high stability in storage, and low sedimentation tendency. Preferably, in a second step, the papercoating slip is prepared from the silanized silica dispersion by addition of binder, preferably polyvinyl alcohol, and of crosslinker, preferably boric acid, and is especially suitable for producing photographic inkjet papers.

The lower the solids content of the formulation, the lower the capacity of the coating lines operated with it, because the volatile constituents of the papercoating compositions (mainly water here) generally have to be removed thermally. The higher the solids content of the formulation, the lower the amount of water which has to be removed and the higher the rate of speed at which the coating lines can be operated. A solids content of >20% by weight, preferably greater than 24% by weight, is desired for papercoating compositions under the conditions selected in example S4. A description of this application can be found in detail in the parallel DE application with the title "Process for preparing a dispersion comprising silicon dioxide particles and cationizing agent".

The composition of the invention can be employed by applying it to a substrate, generally by dipping, spreading, rubbing, spraying, more particularly with droplet sizes below 200 μm, preferably less than 100 μm down into the nanometer range; depositing, spincoating, using curtain coaters, or any other techniques known to the skilled person. To this end, the composition is adjusted to an organosilicon compound concentration suitable for the method employed. Depending on the processing method, therefore, the concentration may range from 0.01% by weight of organosilicon compound to 99.5% by weight in the composition. The methods of application are well known to a person skilled in the pertinent art. In addition, a coating applied to a substrate can cure or bind to the substrate in a conventional manner under ambient conditions and/or via an additionally thermal and/or photochemical treatment. In this way, for example, a composition of the invention can be used to treat organic or inorganic substrates or as an input component in formulations.

The examples below illustrate the present invention, more particularly the process of the invention and also the compositions of the invention, in more detail, without restricting the invention to these examples.

EXAMPLES

Methods of Determination:

Hydrolyzable chloride was titrated potentiographically with silver nitrate (for example, Metrohm, type 682 silver rod as indicator electrode and Ag/AgCl reference electrode or another suitable reference electrode). Total chloride content after Wurtzschmitt digestion. For this purpose, the sample is digested with sodium peroxide in a Wurtzschmitt bomb. After acidification with nitric acid, chloride is measured potentiographically with silver nitrate, as above.

In the case of a complete reaction of the chloroalkyl functionality with tertiary amines, the analytical values for hydrolyzable chloride and total chloride are identical and are therefore a measure of the completeness of the reaction, since the sum total of saltlike chloride (amine hydrochloride) and covalently bonded chlorine (chloroalkyl functionality) is determined by total chloride, and exclusively saltlike chloride or chloride which can be eliminated with water (amine hydrochloride in the present case) is determined by hydrolyzable chloride. At the beginning of the reaction, the value for hydrolyzable chloride is zero and increases at complete conversion to the value which is measured for total chloride. Therefore, these analyses are very useful in addition to $^1$H and $^{13}$C NMR spectroscopy for reaction monitoring.

The alcohol content after hydrolysis is determined by gas chromatography. For this purpose, a sample of a defined amount is hydrolyzed with sulfuric acid (5 g of sample, 25 ml of $H_2SO_4$, w=20%). 75 ml of distilled water are added. Thereafter, neutralization takes place with aqueous sodium hydroxide solution, and a steam distillation is performed. Internal standard: 2-butanol.

Determination of nitrogen, organically bound, ammonium, etc. organically bound nitrogen can be converted into ammonium by means of Kjeldahl digestion and determined acidimetrically as ammonia following addition of aqueous sodium hydroxide solution. Method: up to 5 g of sample are heated with 10 ml of sulfuric acid (concentrated) and a Kjeldahl tablet (Merck 1.15348) until the digestion solution is pale and clear apart from any precipitated silica. The digestion vessel is attached to a distillation apparatus, and ammonia released as a result of addition of aqueous sodium hydroxide solution (27%) is distilled over into the receiver. With addition of boric acid (2%), the ammonia content is titrated with sulfuric acid (c($H_2SO_4$)=0.05 mol/l or 0.005 mol/l). V=consumption of sulfuric acid in ml, c=concentration of sulfuric acid in mol/l, z=number of equivalents of sulfuric acid=2, E=initial mass in mg.

Evaluation:

$$N[\%] = \frac{100 \cdot V \cdot c \cdot z \cdot 14.01}{E}$$

Determination of $SiO_2$ takes place following decomposition using sulfuric acid and Kjeldahl catalyst, by determining the weight of the precipitated $SiO_2$.

Method: The 1 g sample is placed in a 250 ml glass beaker and a Kjeldahl tablet (e.g., Merck #15348) and 20 ml of sulfuric acid (concentrated) are added. The solution is slowly heated. The organic constituents are oxidized, until the digestion solution, with fuming of the sulfuric acid, remains clear and pale. After cooling and after cautious dilution to approximately 200 ml, the precipitated silica is removed by filtration on a white ribbon filter. The filter is washed with water until the pH of the wash water is >4, and then dried and incinerated in a platinum crucible. The residue is ignited at 800° C. and reweighed. After fuming with hydrofluoric acid (concentrated), ignition at 800° C. and reweighing are repeated. m=weight difference before and after fluorination in g; E=initial mass in g.

Evaluation:

$$SiO_2[\%] = \frac{100 \cdot m}{E}$$

Shown below are the DIN standards used in determining the stated parameters:
Solids content: DIN 38409-1 (1987-01-00)
Refractive index: DIN 51423 (2010-02-00)
Density: DIN 51757 (1994-04-00)
Viscosity DIN 53015 (2001-02-00)
Color number DIN EN ISO 6271 (2005-03-00)
Cloudiness DIN EN ISO 7027 (2000-04-00)

Example 1

3-Chloropropyltriethoxysilane (CPTEO)/N,N-Dimethylethanolamine

Apparatus:
4 l stirred reactor with distilling device, pot thermometer, top thermometer, vacuum pump, manometer metering device, and pressure filter Materials Used

| Inputs | m (input) [g] | n (inputs) [mol] | w (inputs) [%] | Comment |
|---|---|---|---|---|
| CPTEO | 1283.0 | 5.328 | 28.79 | M = 240.8 g/mol, bp = 230° C. |
| N,N-Dimethylethanolamine | 570.5 | 6.400 | 12.80 | M = 116.21 g/mol bp = 133° C. |
| Ethanol | 160.0 | | 3.59 | |
| Deionized water: | | | | |
| 1$^{st}$ addition | 143.9 | 7.992 | 3.23 | |
| 2$^{nd}$ addition | 143.9 | | 3.23 | |
| 3$^{rd}$ addition | 143.9 | | 3.23 | |
| 4$^{th}$ addition | 144.5 | | 3.24 | |
| 5$^{th}$-12$^{th}$ addition | 1866.1 | | 41.88 | |
| Σ (inputs) | 4455.8 | | 100.00 | | m(Ethanol from hydrolysis) = 735.3 g

Final Mass of Product:
  2438.5 g (theory: 2562.7 g)
Final Mass of Distillate:
  2236.0 g Procedure:
1. Hydrolysis A 4 l four-neck flask was charged with 1283.0 g of CPTEO (5.328 mol) and 160.0 g of ethanol. At RT, 143.9 g of deionized water (1.5 mol H2O/mol Si) were added dropwise over the course of 16 minutes. During this addition, the pot temperature rose to around 40° C.

2. Quaternization Reaction

Subsequently 570.5 g (6.400 mol) of dimethylethanolamine were stirred in over the course of 6 minutes. During this addition, the pot temperature rose from 40° C. to around 48° C. This was followed by boiling at reflux for around 45 minutes (pot temperature around 85° C.).

3. Distillation at RT/Quaternization Reaction

Under atmospheric pressure, 1706.6 g of water/ethanol/dimethylethanoldiamine were distilled off over the course of around 6 hours. During this time, 2038.3 g of water were stirred in seven portions. After distillation for around 3 hours, a total of 432.4 g of deionized water were introduced in three portions ($2^{nd}$ to $4^{th}$ water addition). A sample of the pot then showed itself to be readily soluble in deionized water.

3. Distillation Under Reduced Pressure

Over the course of 1.7 hours, at a pot temperature of 50 to 55° C. and under an absolute pressure of around 140 mbar, 529.4 g of water/ethanol/dimethylethanoldiamine mixture were distilled off. At the end of the distillation, 560.17 g of deionized water were stirred in. This gave a slightly cloudy/slightly yellowish liquid of low viscosity. Yield: 2521.7 g 4. Filtration Filtration was carried out in a 2 l laboratory pressure filter at RT with an overpressure of around 0.5 bar of N2. The filter used was a cut-to-size filter plate (pilot plant, used for bubble filters) having a diameter of 135 mm. The filtration time was around 20 minutes. Filtration produced a clear, slightly yellowish liquid of low viscosity.

Analysis (Product):

| Determination | Unit | Result | Method |
|---|---|---|---|
| Total N | wt % | 2.9 | see above |
| Total chloride | wt % | 7.4 | see above |
| Hydrolyzable chloride | wt % | 7.0 | see above |
| $SiO_2$ | wt % | 12.5 | see above |
| Solids content | wt % | 47.5 | DIN 38409-H1-1 |
| Ethanol (after hydrolysis) | wt % | <0.1 | see above |
| pH | | 8.6 | |
| Refractive index (20° C.) | | 1.4146 | DIN 51423 |
| Density (20° C.) | g/cm$^3$ | 1.126 | DIN 51757 |
| Viscosity (20° C.) | mPa s | 12.3 | DIN 53015 |
| Flash point | ° C. | >95 | DIN EN ISO 2719 |
| Color number | mg Pt—Co/l | 55 | ISO 6271 |
| Turbidity | TU/F | 0.36 | ISO 7027 |

$^1$H and $^{13}$C NMR:

Purity of the target compound around 95.8 mol %. 4.2 mol % of free dimethylethanolamine. No indications of any transesterification of the aminoethanol group to form SiOR.

$^{29}$Si NMR:

1% Si silane

7% Si M

45% Si D

47% Si T structures

The new product is notable for even better processing and applications properties in the production of high-gloss inkjet photographic papers.

Comments on the Reaction of N,N-Dimethylethanolamine with CPTEO

Differences in the process for the reaction of haloalkylalkoxysilanes with tertiary amines, as in PCT/EP2010/053626.

As set out in example 5, it proves advantageous if the CPTEO is prehydrolyzed prior to the reaction of CPTEO with N,N-dimethylethanolamine, and the hydrolysis alcohol released is removed by distillation.

If there is no prehydrolysis of CPTEO prior to reaction with N,N-dimethylethanolamine, then it proves advantageous to operate with an excess of N,N-dimethylethanolamine, in order to prevent significant precipitation of CPTEO (see example 3). If necessary, excess N,N-dimethylethanolamine can be separated off by distillation.

Incompletely reacted CPTEO with N,N-dimethylethanolamine can be precipitated in principle by addition of water (see example 2).

If the reaction of CPTEO with N,N-dimethylethanolamine is carried out at temperatures of 140 to 150° C., this leads to intense discoloration of the product (see example 4).

Example 2

A 500 ml four-neck flask was charged with 160.01 g of Dynasylan® CPTEO (0.664 mol). At RT, 20.73 g of ethanol were stirred in and then 18.09 g of deionized water (1.5 mol $H_2O$/mol Si) were added dropwise with stirring over the course of 13 minutes. During this addition, the pot temperature rose from 20° C. to 33° C. Subsequently, over the course of two minutes, 59.34 g of N,N-dimethylethanolamine (0.665 mol) were stirred in, leading to an increase in the pot temperature to 42° C. This was followed by boiling under reflux at a pot temperature of around 87° C. for one hour. Thereafter, ethanol mixture was distilled off under atmospheric pressure. In the course of the distillation, the pot temperature reached a maximum temperature of 107° C. 46 minutes after the beginning of distillation, 36.08 g of deionized water were metered in over the course of three minutes. A further 184.88 g of deionized water were added during further distillation. A total of 184.5 g of liquid were removed by distillation. After a total of 7.5 hours, the batch was cooled to RT. The yield was 266.07 g (corresponding to 90.3% of theory) of clear, slightly yellowish liquid of low viscosity. Deposited on the stirrer were significant quantities of a gel-like substance (condensed silane hydrolysate), which was responsible for the relatively low yield (reduced yield as a result of gel deposits).

Analysis:

| Determination | Unit | Result | Method |
|---|---|---|---|
| Total N | wt % | 3.0 | see above |
| Total chloride | wt % | 7.7 | see above |
| Hydrolyzable chloride | wt % | 7.6 | see above |
| Solids content | wt % | 51.5 | DIN 38409-H1-1 |
| Ethanol (after hydrolysis) | wt % | 0.1 | see above |
| pH | | 7.5 | |
| Refractive index (20° C.) | | 1.4180 | DIN 51423 |
| Density (20° C.) | g/cm$^3$ | 1.132 | DIN 51757 |
| Viscosity (20° C.) | mPa s | 14.2 | DIN 53015 |
| Color number | mg Pt—Co/l | 30 | ISO 6271 |
| Turbidity | TU/F | 0.23 | ISO 7027 |

$^1$H and $^{13}$C NMR: 98.2 mol % purity of the quaternary target compound, about 1.8 mol % of free dimethylethanolamine $^{29}$Si NMR: 1% Si silane 7% Si M 47% Si D 45% Si T structures Example 3

20 mol % DMEA Excess, No Gel Deposits

A 500 ml four-neck flask was charged with 160.55 g of Dynasylan® CPTEO (0.667 mol). At RT, 20.12 g of ethanol were stirred in and then 18.05 g of deionized water (1.5 mol $H_2O$/mol Si) were added dropwise with stirring over the course of 13 minutes. During this addition, the pot temperature rose from 21° C. to 28° C. 33.1 g of hydrolysis ethanol were distilled off under reduced pressure (140 to 94 mbar absolute pressure) at a pot temperature of around 35° C. over the course of 45 minutes. Subsequently, over the course of four minutes, 71.34 g of N,N-dimethylethanolamine (0.800 mol) were stirred in, leading to an increase in the pot temperature to 35° C. Thereafter, 80.08 g of ethanol mixture were distilled off over the course of 38 minutes under atmospheric pressure. Boiling under reflux was carried out for 20 minutes at a pot temperature of 96.0 to 92.2° C. Subsequently, 17.99 g of deionized water were metered in over the course of two minutes. A further 245.47 g of deionized water were added during further distillation. A total of 232.5 g of liquid were removed by distillation. After a total of 7.65 hours, the batch was cooled to RT. The yield was 325.9 g (corresponding to 96.0% of theory) of clear, slightly yellowish liquid of low viscosity. No gel deposits in the reaction vessel.

Analysis:

| Determination | Unit | Result | Method |
| --- | --- | --- | --- |
| Total N | wt % | 2.7 | see above |
| Total chloride | wt % | 7.2 | see above |
| Hydrolyzable chloride | wt % | 7.0 | see above |
| Solids content | wt % | 47.2 | DIN 38409-H1-1 |
| Ethanol (after hydrolysis) | wt % | <0.1 | see above |
| pH | | 8.0 | |
| Refractive index (20° C.) | | 1.4121 | DIN 51423 |
| Density (20° C.) | g/cm³ | 1.122 | DIN 51757 |
| Viscosity (20° C.) | mPa s | 10.9 | DIN 53015 |
| Color number | mg Pt—Co/l | 25 | ISO 6271 |
| Turbidity | TU/F | 1.0 | ISO 7027 |

$^1$H and $^{13}$C NMR: 97.3 mol % purity of the quaternary target compound, about 2.7 mol % of free dimethylethanolamine $^{29}$Si NMR: –% Si silane
6% Si M
47% Si D
47% Si T structures Example 4

CPTEO/N,N-Dimethylethanolamine (DMAE) Reaction at 140 to 150° C.

A 500 ml four-neck flask was charged with 160.10 g of CPTEO (0.665 mol). At a pot temperature of 20° C., 59.35 g of N,N-dimethylethanolamine (0.666 mol) were stirred in. At a pot temperature of 140.6 to 151.8° C., stirring was carried out for 6.8 hours. After a reaction time of around 2.5 hours, GC analysis still indicated 14.0 area % of CPTEO and <0.1 area % of N,N-dimethylethanolamine in the pot. The pot contents had in the meantime undergone a change in color from slightly yellowish through orange to red. After a reaction time of 3.7 hours, GC analysis of the pot sample indicated a CPTEO content of 16.8 area %. At this point 13.98 g of N,N-dimethylethanolamine (0.157 mol) were metered in. The pot contents changed color to brown. After a reaction time of a further 22 minutes, the GC analysis of the pot contents still indicated 7.4 area % of CPTEO. A further 13.99 g of N,N-dimethylethanolamine (0.157 mol) were metered in. After a reaction time of a further 13 minutes, GC analysis still indicated 3.2 area % of CPTEO in the pot contents. 127.55 g of deionized water were then metered in over the course of 31 minutes. After a total of 8 hours, the batch was cooled to RT. The pot contents were virtually clear and brown. The next day, free ethanol was distilled off under reduced pressure (300 mbar to 176 mbar absolute pressure) at a pot temperature of 61.1 to 76.9° C. In total, over around 4 hours, 230.28 g of liquid were removed by distillation. During the distillation, 223.8 g of deionized water were metered in. The yield was 348.19 g (corresponding to 95.4% of theory) of clear brown liquid of low viscosity. No gel deposits in the reaction vessel.

Analysis:

| Determination | Unit | Result | Method |
| --- | --- | --- | --- |
| Total N | wt % | 3.1 | see above |
| Total chloride | wt % | 6.6 | see above |
| Hydrolyzable chloride | wt % | 6.3 | see above |
| Solids content | wt % | 45.7 | DIN 38409-H1-1 |
| Ethanol (after hydrolysis) | wt % | <0.1 | see above |
| pH | | 9.5 | |
| Refractive index (20° C.) | | 1.1429 | DIN 51423 |
| Density (20° C.) | g/cm³ | 1.145 | DIN 51757 |
| Viscosity (20° C.) | mPa s | 11.1 | DIN 53015 |
| Color number | Gardner | 8 | ISO 6271 |
| Turbidity | TU/F | 1.6 | ISO 7027 |

Example 5

CPTEO/DMAE 1:1 (Mol), CPTEO Prehydrolyzed with 1.5 Mol of $H_2O$/Mol of Si

A 4 l three-neck flask was charged with 829.30 g of CPTEO (3.444 mol) and 100.40 g of ethanol were stirred in at a pot temperature of 22° C. Subsequently, at room temperature and with intense stirring, 93.12 g of deionized water were metered in over the course of 8 minutes. During this addition, the pot temperature rose to 47° C. Under reduced pressure, the hydrolysis ethanol was then distilled off until the pot temperature was 62.2° C. and the absolute pressure was <1 mbar. Subsequently, 307.12 g (3.445 mol) of N,N-dimethylethanolamine were stirred in. During this addition, the pot temperature rose to a maximum of 58.5° C. The pot contents were subsequently heated to 109.4° C., and 93.05 g of water were metered in cautiously over the course of 11 minutes. After 12 minutes there was a further addition of water (92.75 g in 6 minutes). Distillative removal of ethanol was commenced, under atmospheric pressure. Subsequently more deionized water, in two portions (92.99 g and 93.01 g), was metered in, and then, under reduced pressure, residual free ethanol was distilled off. During the vacuum distillation and after the end of the distillation, a total of a further 956.36 g of deionized water were stirred into the reaction mixture. This gave 1773.2 g (97.0%) of slightly cloudy/yellowish liquid of low viscosity.

Analysis:

| Determination | Unit | Result | Method |
| --- | --- | --- | --- |
| Total N | wt % | 2.6 | see above |
| Total chloride | wt % | 6.8 | see above |
| Hydrolyzable chloride | wt % | 6.5 | see above |
| Solids content | wt % | 43.9 | DIN 38409-H1-1 |
| Ethanol (after hydrolysis) | wt % | <0.1 | see above |
| pH | | 6.3 | |
| Refractive index (20° C.) | | 1.4059 | DIN 51423 |
| Density (20° C.) | g/cm³ | 1.115 | DIN 51757 |
| Viscosity (20° C.) | mPa s | 8.7 | DIN 53015 |
| Color number | mgPt—Co/l | 60 | ISO 6271 |
| Turbidity | TU/F | 2.7 | ISO 7027 |

Comparative Example for the Preparation of Dispersions

Quaternary silane system (CPTEO/TMEDA), prepared from 3-chloropropyltriethoxysilane (CPTEO) and tetramethylethylenediamine (TMEDA).

Comparative Example 1

Water-based, VOC-free solution of a quaternary silane system, prepared from 3-chloropropyltriethoxysilane (CPTEO) and tetramethylethylenediamine (TMEDA).

Apparatus: Stirred reactor with distilling device, pot thermometer, top thermometer, vacuum pump, manometer, and metering device Materials Used:

| Inputs | M (input) [g] | N (inputs) [mol] | w (inputs) [%] | Comment |
|---|---|---|---|---|
| Chloropropyl-triethoxysilane | 3206.2 | 13.31 | 37.3 | M = 240.8 g/mol |
| N,N,N',N'-Tetramethyl-ethylenediamine | 1547.2 | 13.31 | 18.0 | M = 116.21 g/mol |
| Deionized water: | | | | |
| 1. Addition | 1603.1 | | 18.6 | |
| 2. Addition | 641.3 | | 7.5 | |
| 3. Addition | 1600.0 | | 18.6 | |
| Σ (inputs) | 8597.8 | | | | m(ethanol from hydrolysis)=1836.8 g; final mass of product after filtration: 6521.4 g (theory: 6761.1 g); final mass of distillate: 2946.5 g Procedure:

1. Reaction (duration about 9.7 h): chloropropyltriethoxysilane was introduced initially and tetramethylethylenediamine was added rapidly with stirring. This was followed by the 1$^{st}$ addition of water within around 20 minutes (volume flow rate around 4.8 l/h) under vigorous stirring. The pot contents were at this point distinctly cloudy, and were heated under reflux (around 87° C.) for 6 hours. The 2$^{nd}$ addition of water was made over the course of 10 minutes to the now clarified pot contents (volume flow rate around 3.9 l/h). After a further 1.5 hours of heating under reflux, the 3$^{rd}$ addition of water was made with stirring (over the course of around 20 minutes, volume flow rate around 4.8 l/h).

2. Distillation (duration about 9 h): At a pot temperature of 49° C. to 54° C., hydrolysis ethanol was distilled off under reduced pressure (100-270 mbar). Following distillative removal of around 1700 g of ethanol/water mixture, 327 g of water were rapidly added. In order to remove the hydrolysis alcohol by distillation almost to completion, it was necessary to remove an at least 60% excess (based on the mass of hydrolysis ethanol) by distillation. The amount of water removed by distillation was returned at the end of the distillation.

3. Filtration (duration around 1 h): Thereafter, the yellowish, slightly cloudy product was filtered via pressure filter (2 l) and Seitz 500 depth filter at an overpressure of 0.8 bar (filtration performance at $d_{filter}$=14 cm: 18 l/h). A clear, slightly yellowish liquid was obtained.

Analyses:

| Determination | Result | Theory | Method |
|---|---|---|---|
| Viscosity (20° C.) [mPa s] | 70 | | DIN 53015 |
| Density (20° C.) [g/ml] | 1.107 | | DIN 51757 |
| Refractive index (20° C.) | 1.4224 | | DIN 51423 |
| Color [mg Pt—Co/l] | 75 | | |
| Solids [%] | 48.4 | | DIN 38409-1 |
| pH | 8.6 | | 1:1 in Wasser, DIN 38404-C5 |
| SiO$_2$ [%] | 11.8 | 11.8 | see above |
| Ethanol after hydrolysis [%] | 0.5 | | see above |
| Total N [%] | 5.0 | 5.5 | see above |
| Total chloride [%] | 7.2 | 7.0 | see above |
| Hydrolyzable chloride [%] | 7.1 | 7.0 | see above |

NMR: $^{13}$C NMR: around 15% of the TMEDA groups were present in the form of the bis adduct. Per 100 SiCH$_2$ groups there was 8 mol % of free TMEDA.

$^{29}$Si NMR: 2.5 Si-% silane; 14.6 Si-% M structures; 49.7 Si-% D structures; 33.3 Si-% T structures Preparation of Dispersions Dispersion examples D1 to D4 below were developed with the proviso that the dispersions should be able to be applied in low-viscosity form and should have similar performance in papercoating in respect of pore structure and pore volume. The measure which emerged for the porosity of the coating was the average aggregate size in the dispersion, measured by dynamic light scattering. For optimum results, an average aggregate size of 140 to 160 nm was desirable. Within a system, higher degrees of fill during dispersing resulted in a decrease in the average particle size. The examples show that by using the silane system of the invention it is possible to realize very high levels of fill while at the same time retaining the desired aggregate size.

Example D1

Dispersion Based on Fumed Silica with a Specific Surface Area of 300 m2/g and Poly-Diallyldimethylammonium Chloride (p-DADMAC) (Comparative Example)

1350 g of deionized water were admixed with 60 g of p-DADMAC. Then 320 g of fumed silica were incorporated with stirring by means of a dissolver at 1500 to 4000 rpm, followed by further preliminary dispersing over a period of 5 minutes at 2000 rpm. Dispersion then continued with cooling (<30° C.) for ten minutes, now using a rotor-stator dispersing apparatus at 15 000 rpm. To conclude, the dispersion was filtered through a 500 μm sieve.

Example D2

Dispersion Based on Fumed Silica with a Specific Surface Area of 300 m2/g and N-Butylaminopropyltrimethoxysilane (Comparative Example)

1200 g of deionized water were admixed with 425 g of fumed silica, incorporated by stirring by means of a dissolver at 1500 to 4000 rpm, followed subsequently by further predispersing over a period of 5 minutes at 2000 rpm. Dispersion then continued with cooling (<30° C.) for ten minutes, now using a rotor-stator dispersing apparatus at 15 000 rpm. Stirring was then carried out again with the dissolver at 2000 rpm, and a mixture of 21.3 g of N-butylaminopropyltrimethoxysilane, 67 g of methanol, and 20 g of formic acid (50 percent strength solution in water) was added, followed by final dispersion for 60 minutes in the rotor-stator system at 5000 rpm at 60° C. To conclude, the dispersion was cooled and filtered through a 500 μm sieve.

Example D3

Dispersion Based on Fumed Silica with a Specific Surface Area of 300 m2/g and Quaternary Silane System (CPTEO/TMEDA) (Comparative Example)

509 g of fumed silica were incorporated by stirring with a dissolver at 1500 to 5000 rpm into a mixture of 1215 g of deionized water, 53.0 g of quaternary silane system (CPTEO/TMEDA system from comparative example 1), and 23.4 g of acetic acid (25 percent strength by weight solution in water), and dispersing was continued at 2000 rpm for 5 minutes. This was followed by final dispersing with a rotor-stator dispersing apparatus (Kinematica Polytron PT6100) over a period of 30 minutes at 10 000 rpm. To conclude, the dispersion was cooled and filtered through a 500 μm sieve.

Example D4

Inventive Dispersion Based on Fumed Silica with a Specific Surface Area of 300 m2/g and the Solution from Example 1

428 g of fumed silica were incorporated by stirring with a dissolver at 1500 to 5000 rpm into a mixture of 805 g of deionized water and 47.4 g of the solution from example 1, and dispersing was continued at 2000 rpm for 10 minutes. This was followed by dispersing with a rotor-stator dispersing apparatus (Kinematica Polytron PT6100) over a period of 30 minutes at 10 000 rpm. To conclude, the dispersion was filtered through a 500 μm sieve.

TABLE

Physicochemical data of dispersions D1 to D4

|  |  | Comparison | | | Invention |
| --- | --- | --- | --- | --- | --- |
|  |  | D1 | D2 | D3 | D4 |
| Solids content*) | % by wt. | 20.0 | 25.0 | 30.0 | 35.0 |
| Particle diameter**) | nm | 157 | 154 | 156 | 148 |
| Viscosity***) | mPa s | 47 | 80 | 122 | 142 |

*)after drying to constant weight at 125° C.;
**)by dynamic light scattering (Horiba LB-500);
***)at 1000 1/s; 23° C.;

Dispersion examples D5 to D8 showed the maximum solids content possible with the respective cationizing additive, independently of the parameter of aggregate size. As expected, the dispersions had very high viscosities, but were still liquid and processable. On account of the small particle sizes, further processing to papercoating slips and inkjet papers was not undertaken.

Example D5

Dispersion Based on Fumed Silica with a Specific Surface Area of 300 m2/g and Poly-Diallyldimethylammonium Chloride (p-DADMAC) (Comparative Example)

1190 g of deionized water were admixed with 60 g of p-DADMAC. Then 320 g of fumed silica were incorporated with stirring by means of a dissolver at 1500 to 4000 rpm, followed by further preliminary dispersing over a period of 5 minutes at 2000 rpm. Dispersion then continued with cooling (<30° C.) for ten minutes, now using a rotor-stator dispersing apparatus at 15 000 rpm. To conclude, the dispersion was filtered through a 500 μm sieve.

Example D6

Dispersion Based on Fumed Silica with a Specific Surface Area of 300 m2/g and N-Butylaminopropyltrimethoxysilane (Comparative Example)

1035 g of water were introduced and 21.2 g of N-butylaminopropyltrimethoxysilane were stirred into the water. After a hydrolysis time of 30 minutes, the initial solution was adjusted to a pH of 4.2 using 63.7 g of acetic acid (25 percent strength by weight solution in water). Then 423.9 g of fumed silica were incorporated by stirring with a dissolver at 1500 to 4000 rpm, followed by further predispersing over a period of five minutes at 2000 rpm. After that, final dispersion took place with cooling (<30° C.) for 30 minutes, now using a rotor-stator dispersing apparatus at 10 000 rpm. To conclude, the dispersion was filtered through a 500 μm sieve.

Example D7

Dispersion Based on Fumed Silica with a Specific Surface Area of 300 m2/g and Quaternary Silane System (CPTEO/TMEDA System from Comparative Example 1) (Comparative Example)

560 g of fumed silica were incorporated by stirring with a dissolver at 1500 to 5000 rpm into a mixture of 1156 g of deionized water, 58.3 g of quaternary silane system (CPTEO/TMEDA), and 25.7 g of acetic acid (25 percent strength by weight solution in water), and dispersing was continued at 2000 rpm for 5 minutes. This was followed by final dispersing with a rotor-stator dispersing apparatus (Kinematica Polytron PT6100) over a period of 30 minutes at 10 000 rpm. To conclude, the dispersion was cooled and filtered through a 500 μm sieve.

Example D8

Inventive Dispersion Based on Fumed Silica with a Specific Surface Area of 300 m2/g and the Solution from Example 1

557 g of fumed silica were incorporated by stirring with a dissolver at 1500 to 5000 rpm into a mixture of 885 g of deionized water and 58 g of the solution from example 1, and dispersing was continued at 2000 rpm for 10 minutes. This was followed by dispersing with a rotor-stator dispersing apparatus (Kinematica Polytron PT6100) over a period of 30 minutes at 10 000 rpm. To conclude, the dispersion was filtered through a 500 μm sieve.

TABLE

Physicochemical data of dispersions D5 to D8

|  |  | Comparison | | | Invention |
|---|---|---|---|---|---|
|  |  | D5 | D6 | D7 | D8 |
| Solids content*[)] | % by wt. | 22.0 | 30 | 33 | 39 |
| Particle diameter**[)] | nm | 132 | 125 | 121 | 114 |
| Viscosity***[)] | mPa s | 5600 | 2800 | 3580 | 5380 |

*[)]after drying to constant weight at 125° C.;
**[)]by dynamic light scattering (Horiba LB-500);
***[)]at 1000 1/s; 23° C.;

Besides fumed silica with a specific surface area (BET surface area 300 m2/g), it is also possible to prepare dispersions of the invention on the basis of other fumed silicas with a specific surface area, as shown by examples D9 to D12.

Examples D9 to D12

General Preparation Instructions (for Quantities See Table)

The fumed silica powder was incorporated by stirring with a dissolver at 1500 to 5000 rpm into a mixture of 885 g of deionized water and the corresponding amount of the solution from example 1, and dispersion continued at 2000 rpm for 10 minutes. Then a rotor-stator dispersing apparatus (Kinematica Polytron PT6100) was used for dispersing at 10 000 rpm over a period of 30 minutes. To conclude, the dispersion was filtered through a 500 µm sieve.

TABLE

Preparation parameters and physicochemical data of dispersions D9 to D12

|  |  | D9 | D10 | D11 | D12 |
|---|---|---|---|---|---|
| Fumed silica type (BET) | m2/g | 150 | 200 | 255 | 255 |
| Quantity of fumed silica used | g | 472 | 375 | 335 | 420 |
| Quantity of solution from example 1 used | g | 26.1 | 27.7 | 31.5 | 39.5 |
| Solids content*[)] | % by wt. | 35 | 30.2 | 28 | 32.6 |
| Particle diameter**[)] | nm | 159 | 150 | 145 | 140 |
| Viscosity***[)] | mPa s | 68 | 58 | 45 | 125 |

*[)]after drying to constant weight at 125° C.;
**[)]by dynamic light scattering (Horiba LB-500);
***[)]at 1000 1/s; 23° C.;

Production of Papercoating Slips

Example S1 (Comparative Example)

By means of a dissolver at 500 rpm, dispersion D1 was admixed with a 12 percent strength by weight solution of polyvinyl alcohol PVA 235, from Kuraray Europe, and the system was stirred for 10 minutes. The amount of PVA 235 added was such as to produce a ratio of silicon dioxide to PVA (dry) of 5:1 (or 6:1 for S9 and S10). To adjust the viscosity, water was added in an amount such as to give the solids content indicated in the table. Then a 7 percent strength by weight solution of boric acid in water was added. The amount of the boric acid was 12.5% by weight of the amount of the polyvinyl alcohol. Lastly, the glyoxal-containing composition "Cartabond TSI" from Clariant was added. The amount corresponded to 4.8% by weight of the amount of the polyvinyl alcohol.

The viscosity of the inkjet papercoating slip was measured using a Brookfield viscometer after 24 hours.

Examples S2, S3, S4, and S9 to S12 were produced in the same way as for S1, but using the respective dispersions D2, D3, D4, and D9 to D12. The solids contents and viscosities of the papercoating slips are reproduced in table 4.

TABLE 3

Solids contents and viscosities of papercoating slips S1 to S4

|  |  | Comparative example | | | as per invention |
|---|---|---|---|---|---|
| from |  | S1 D1 | S2 D2 | S3 D3 | S4 D4 |
| Solids content | % by wt. | 17.5 | 22.6 | 23.1 | 24.3 |
| Viscosity*[)] | mPa s | 3680 | 5350 | 3410 | 3200 |

*[)]Viscosity (Brookfield) at 100 rpm and 20° C.; measured after 24 h

TABLE 4

Solids contents and viscosities of papercoating slips S9-S12 as per invention

|  |  | S9 | S10 | S11 | S12 |
|---|---|---|---|---|---|
| from |  | D9 | D10 | D11 | D12 |
| Solids content | % by wt. | 25.1 | 24.3 | 22.9 | 23.1 |
| Viscosity*[)] | mPa s | 4210 | 2860 | 3410 | 2200 |

Production of the Inkjet Coating

Inventive papercoating slips S4 and S9 to S12 were applied to a photographic base paper (thickness 300 µm) using a profiled doctor bar. The wet film thickness of the papercoating slip was 80 µm. The coating was dried at 105° C. over a period of 8 minutes. The application weight achieved was a uniform 22 g/m². The coated papers were printed on a Canon PIXMA iP6600D inkjet printer with very high resolution. The evaluation of the print outcomes is reproduced in table 5.

TABLE 5

Evaluation*[)] of the print outcomes

|  | S1 | S2 | S3 | S4 | S9 | S10 | S11 | S12 |
|---|---|---|---|---|---|---|---|---|
| Slip intensity | 2 | 2 | 2 | 2 | 3 | 2.5 | 2 | 2 |
| Resolution | 2.5 | 2 | 2 | 2 | 3 | 3 | 2.5 | 2 |
| Slip flow**[)] | 1.5 | 1 | 1 | 1 | 3 | 2.5 | 2 | 2.5 |
| Slip shift | 1.75 | 1.5 | 1.5 | 1.5 | 3 | 2.5 | 1.75 | 1.5 |
| Gloss***[)] | 45.1 | 43.5 | 43.1 | 45.3 | 30.1 | 39.8 | 42.3 | 45.3 |

*[)]Best score 1, worst score 6;
**[)]bleeding;
***[)]at 60° viewing angle

The invention claimed is:

1. A quaternary-amino alcohol-functional, organosilicon compound, comprising
 a quaternary-amino alcohol-functional silanol and a quaternary-amino alcohol-functional siloxanol oligomer with Si—O-crosslinked structural elements, which form catenate, cyclic and/or crosslinked structures and which are obtainable from a reaction of at least one silane of the formulae II, IV or at least one hydrolysis, condensation or co-condensation product starting from silanes of the formula II and/or IV, water and at least one amino alcohol of the formula III and optionally the hydrolysis alcohol formed in this reaction is at least partly removed from the system, where at least one structure of said quaternary-amino alcohol-functional, organosilicon compounds is represented by general formula I,

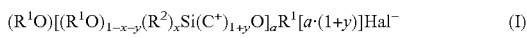

$(R^1O)[(R^1O)_{1-x-y}(R^2)_xSi(C^+)_{1+y}O]_aR^1[a\cdot(1+y)]Hal^-$ (I)

where $C^+$ in formula I is independently a group of the formula V

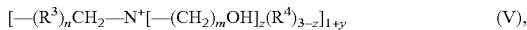

$[—(R^3)_nCH_2—N^+[—(CH_2)_mOH]_z(R^4)_{3-z}]_{1+y}$ (V), wherein, in formula I,
each $R^1$ is, independently, hydrogen or a linear, branched or cyclic alkyl group having 1 to 8 C atoms,
each $R^2$ is, independently, a linear, branched or cyclic alkyl group having 1 to 8 C atoms or is an aryl, arylalkyl or acyl group,
wherein, in formula V
each $R^3$ is, independently, a linear, branched or cyclic alkylene group having 1 to 18 C atoms,
each $R^4$ is, independently, a group comprising from 1 to 16 carbon atoms, wherein, in formulae I and V, independently, n is 0 or 1, m is an integer between 1 and 16 and z is 1 or 2 or 3, and Hal is chloro or bromo, and x is 0 or 1, y is 0 or 1 and (x+y) is 0 or 1,
and a is greater than or equal to 1,
where the silane of formula II is a haloalkylsilane,

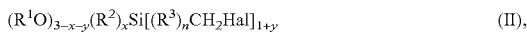

$(R^1O)_{3-x-y}(R^2)_xSi[(R^3)_nCH_2Hal]_{1+y}$ (II), and the silane of the formula IV is a quaternary-amino alcohol-functional silane:

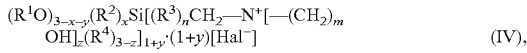

$(R^1O)_{3-x-y}(R^2)_xSi[(R^3)_nCH_2—N^+[—(CH_2)_m OH]_z(R^4)_{3-z}]_{1+y}\cdot(1+y)[Hal^-]$ (IV), and the amino alcohol corresponds to the formula III,

$[HO—(CH_2)_m—]_zN(R^4)_{3-z}$ (III), wherein, in formulae II, III and IV, each $R^1$ is, independently, a hydrogen, a linear, branched or cyclic alkyl group having 1 to 8 carbon atoms, or an aryl, arylalkyl or acyl group,
each $R^2$, independently, is a linear, branched or cyclic alkyl group having 1 to 8 C atoms or is an aryl, arylalkyl or acyl group,
$R^3$, $R^4$, Hal and also n, m and z, independently of one another, are as defined above, and x is 0, 1 or 2, y is 0, 1 or 2 and (x+y) is 0, 1 or 2.

2. A composition comprising a quaternary-amino alcohol-functional, organosilicon compound according to claim 1, and water, obtainable by a process that comprises:
reacting, as component A
(i) at least one haloalkyl-functional alkoxysilane of general formula II

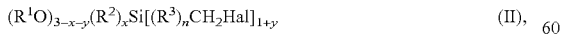

$(R^1O)_{3-x-y}(R^2)_xSi[(R^3)_nCH_2Hal]_{1+y}$ (II), wherein
each $R^1$ is identical or different and is a hydrogen, a linear, branched or cyclic alkyl group having 1 to 8 carbon atoms, or an aryl, arylalkyl or acyl group,
each $R^2$ is identical or different and is a linear, branched or cyclic alkyl group having 1 to 8 carbon atoms or is an aryl, arylalkyl or acyl group,
each $R^3$ is identical or different and is a linear, branched or cyclic alkylene group having 1 to 18 carbon atoms,
n is 0 or 1 and Hal is chloro or bromo,
and x is 0, 1 or 2, y is 0, 1 or 2 and (x+y) is 0, 1 or 2,
or
(ii) a hydrolysis or condensation product of at least one alkoxysilane of the aforementioned general formula II
or
(iii) a mixture of at least one alkoxysilane of the aforementioned general formula II and a hydrolysis and/or condensation product of at least one alkoxysilane of the aforementioned general formula II
with an amino alcohol of general formula III as component B,

$[HO—(CH_2)_m—]_zN(R^4)_{3-z}$ (III), in which each $R^4$ is identical or different and is a group comprising 1 to 16 carbon atoms, m is an integer between 1 and 16 and z is 1 or 2 or 3,
carrying out at least a part of the process in the presence of a defined amount of water, and optionally removing the resultant hydrolysis alcohol at least partly from the system.

3. The composition as claimed in claim 2, wherein
the reaction of component A and of component B is carried out in the presence of a defined amount of water, or component A is reacted with component B and the product is subsequently hydrolyzed in the presence of a defined amount of water.

4. The composition as claimed in claim 2, wherein component B is at least one member selected from the group consisting of N,N-dimethylethanolamine, N,N-diethylethanolamine, N-methyldiethanolamine, N-ethyldiethanolamine, and N-triethanolamine.

5. The composition as claimed in claim 2, wherein water is present in an amount of 0.5 to 500 mol of water per mole of silicon atoms present in component.

6. The composition as claimed in claim 2, wherein the water is metered continuously or discontinuously to component A, optionally in a mixture with component B, or to the quaternary-amino alcohol-functional, organosilicon compound of formula IV

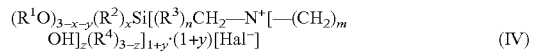

$(R^1O)_{3-x-y}(R^2)_xSi[(R^3)_nCH_2—N^+[—(CH_2)_m OH]_z(R^4)_{3-z}]_{1+y}\cdot(1+y)[Hal^-]$ (IV)

that is formed, the water added discontinuously with stirring where in formula IV $R^1$, $R^2$, $R^3$, $R^4$, x, y, z, n and m have the above-defined definition.

7. The composition as claimed in claim 2, wherein portionwise in each case, the defined amount of water is 0.5 to 4.0 mol of water per mole of silicon atoms.

8. The composition as claimed in claim 2, wherein
the reaction is carried out in the presence of a solvent selected from the group consisting of an alcohol formed in the hydrolysis of the compound of the formula II ethanol, methanol, n-propanol, and isopropanol.

9. The composition as claimed in claim 2, wherein the reaction is carried out under a pressure of 1 mbar to 100 bar and at a temperature of 20 and 150° C.

10. The composition as claimed in claim 2, wherein the process further comprises removing
volatile solvent and optionally groups which can be hydrolyzed to volatile solvent, to a level in the overall composition of below 12% by weight to 0% by weight wherein said removing can be carried out during the reaction, after the reaction, or both, thereafter by distillation.

11. The composition as claimed in claim 2, wherein component A is at least one member selected from the group consisting of 3-chloropropyltrimethoxysilane, 3-chloropropyltriethoxysilane, 3-chloropropylmethyldimethoxysilane, 3-chloropropylmethyldiethoxysilane, 3-chloropropyldimethylethoxysilane, 3-chloropropyldimethylmethoxysilane, and or of a hydrolysis or condensation product of the aforementioned alkoxysilanes.

12. The composition as claimed in claim 2, wherein components A and B are present, in relation to the haloalkyl group of component A and to the tertiary nitrogen of component B, in a molar ratio of 2:1 to 1:100.

13. The composition as claimed in claim 2, wherein said reacting is carried out by
a) component A together with a solvent and adding a defined amount of water, thereafter
adding component B,
removing hydrolysis alcohol at least partly from the system, and adding water in defined amounts,
or
b) introducing component A and adding a solvent, thereafter
adding a defined amount of water, therafter
adding component B,
removing hydrolysis alcohol at least partly from the system, and adding water in defined amounts,
or
c) introducing component A and adding a solvent,
adding a defined amount of water,
removing hydrolysis alcohol at least partly from the system,
thereafter adding component B, and
removing hydrolysis alcohol at least partly from the system,
adding a defined amount of water and
removing hydrolysis alcohol at least partly from the system, and adding water in defined amounts,
or
d) reacting component A with component B at elevated temperature,
adding an additional amount of component B, and
subsequently adding a defined amount of water, forming hydrolysis alcohol at least partly from the system, and adding water in defined amounts,
or
e) introducing component A and adding a solvent,
adding a defined amount of water and
removing hydrolysis alcohol at least partly from the system,
subsequently adding component B and
adding, at elevated temperature, a defined amount of water, and
removing hydrolysis alcohol at least partly from the system, and optionally adding water in defined amounts,
or
f) introducing component A together with a solvent and adding a defined amount of water,
removing hydrolysis alcohol at least partly from the system,
adding component B, and
removing hydrolysis alcohol at least partly from the system,
and adding water in defined amounts.

14. The composition as claimed in claim 2, wherein the composition has a viscosity of less than 1500 mPa s.

15. The composition as claimed in claim 2, which has
a solids content in the composition of 0.1% to 99.9% by weight with all of the constituents in the composition making 100% by weight in total.

16. The composition as claimed in claim 2, which has
a total nitrogen content of 0.1% to 15% by weight for a viscosity of 1 to 100 mPa s, and optionally for a pH in the range from 5.0 to 11.0.

17. The composition as claimed in claim 2, wherein the composition further comprises at least one selected from the group consisting of a pigment, a filler, a binder, a crosslinker, an optical brightener, a coating auxiliary, and another auxiliary.

* * * * *